United States Patent
Auvray et al.

(10) Patent No.: US 11,816,838 B2
(45) Date of Patent: Nov. 14, 2023

(54) INTRAVASCULAR ULTRASOUND IMAGING

(71) Applicant: KONINKLIJKE PHILIPS N.V., Eindhoven (NL)

(72) Inventors: Vincent Maurice André Auvray, Meudon (FR); Raoul Florent, Ville d'Avray (FR); Antoine Collet-Billon, Paris (FR); Benoit Jean-Dominique Bertrand Maurice Mory, Medford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 306 days.

(21) Appl. No.: 17/279,149

(22) PCT Filed: Sep. 25, 2019

(86) PCT No.: PCT/EP2019/075873
§ 371 (c)(1),
(2) Date: Mar. 24, 2021

(87) PCT Pub. No.: WO2020/064841
PCT Pub. Date: Apr. 2, 2020

(65) Prior Publication Data
US 2021/0390698 A1    Dec. 16, 2021

(30) Foreign Application Priority Data
Sep. 26, 2018  (EP) ..................................... 18290108

(51) Int. Cl.
*G06K 9/00*     (2022.01)
*G06T 7/00*     (2017.01)
(Continued)

(52) U.S. Cl.
CPC ............ *G06T 7/0016* (2013.01); *G06T 5/003* (2013.01); *G06T 7/20* (2013.01); *G06T 7/30* (2017.01);
(Continued)

(58) Field of Classification Search
None
See application file for complete search history.

(56) References Cited

U.S. PATENT DOCUMENTS

| | | | |
|---|---|---|---|
| 5,997,479 | A | 12/1999 | Savord |
| 6,013,032 | A | 1/2000 | Savord |

(Continued)

FOREIGN PATENT DOCUMENTS

| | | |
|---|---|---|
| CN | 102509267 B | 11/2013 |
| WO | 2012014212 A2 | 2/2012 |
| WO | 2016140116 A1 | 9/2016 |

OTHER PUBLICATIONS

Wang, Peng, et al. "Image-based co-registration of angiography and intravascular ultrasound images." IEEE transactions on medical imaging 32.12 (2013): 2238-2249.*

(Continued)

*Primary Examiner* — Andrew M Moyer
*Assistant Examiner* — Owais Iqbal Memon

(57) ABSTRACT

An image processing apparatus (10) is disclosed that comprises a processor arrangement (16) adapted to receive image data corresponding to a region of interest (1) of a patients cardiovascular system, said image data comprising a temporal sequence (15) of intravascular ultrasound images acquired (150) at different phases of at least one cardiac cycle of said patient, said intravascular ultrasound images imaging overlapping volumes of the patient's cardiovascular system; implement a spatial reordering process of said temporal sequence of intravascular ultrasound images by (Continued)

evaluating the image data to select at least one spatial reference (6, Vref) associated with said temporal sequence of intravascular ultrasound images; estimating a distance to the at least one spatial reference for each of the intravascular ultrasound images of said temporal sequence; and reordering said temporal sequence of intravascular ultrasound images into a spatial sequence of intravascular ultrasound images based on the estimated distances; and generate an output comprising said spatial sequence of intravascular ultrasound images. Also disclosed are a method and computer program product to configure an image processing apparatus accordingly.

20 Claims, 10 Drawing Sheets

(51) Int. Cl.
  *G06T 7/55* (2017.01)
  *G06T 7/30* (2017.01)
  *G06T 5/00* (2006.01)
  *G06T 7/20* (2017.01)

(52) U.S. Cl.
  CPC ...... *G06T 7/55* (2017.01); *G06T 2207/10028* (2013.01); *G06T 2207/10121* (2013.01); *G06T 2207/10132* (2013.01); *G06T 2207/30101* (2013.01)

(56) References Cited

U.S. PATENT DOCUMENTS

| | | | |
|---|---|---|---|
| 6,283,919 B1 | 9/2001 | Roundhill | |
| 6,443,896 B1 | 9/2002 | Detmer | |
| 6,458,083 B1 | 10/2002 | Jago | |
| 6,530,885 B1 | 3/2003 | Entrekin | |
| 6,623,432 B2 | 9/2003 | Powers | |
| 8,554,308 B2 | 10/2013 | Florent | |
| 2007/0038081 A1 | 2/2007 | Eck | |
| 2010/0160764 A1* | 6/2010 | Steinberg | G16H 50/30 600/407 |
| 2012/0004537 A1* | 1/2012 | Tolkowsky | A61B 8/12 600/424 |
| 2012/0059253 A1* | 3/2012 | Wang | A61B 6/5247 600/427 |
| 2015/0131886 A1 | 5/2015 | Aben | |

OTHER PUBLICATIONS

Khalil, Azira, et al. "An overview on image registration techniques for cardiac diagnosis and treatment." Cardiology research and practice 2018 (2018).*
Shi, Chaoyang, et al. "Three-dimensional intravascular reconstruction techniques based on intravascular ultrasound: A technical review." IEEE journal of biomedical and health informatics 22.3 (2017): 806-817.*
Yu, Mingyue, et al. "Intravascular ultrasound imaging with virtual source synthetic aperture focusing and coherence factor weighting." IEEE transactions on medical imaging 36.10 (2017): 2171-2178.*
Barajas, Joel, et al. "Cardiac phase extraction in IVUS sequences using 1-D gabor filters." 2007 29th Annual International Conference of the IEEE Engineering in Medicine and Biology Society. IEEE, 2007. (Year: 2007).*
Matsumoto, Monica MS, et al. "Cardiac phase detection in intravascular ultrasound images." Medical Imaging 2008: Ultrasonic Imaging and Signal Processing. vol. 6920. SPIE, 2008. (Year: 2008).*
International Search Report and Written Opinion of PCT/EP2019/075873, dated Dec. 6, 2019.
Hernandez, Aura et al "Image-based ECG Sampling of IVUS Sequences" 2008 IEEE Ultrasonics Symposium.
Wang et al "Image-Based Co-Registration of Angiography and Intravascular Ultrasound Images", IEEE Transactions on Medical Imaging, vol. 32, No. 12, 2013, pp. 2238-2249.
Arbab-Zadeh, A. et al "Axial Movement of the Intravascular Ultrasound Probe During the Cardiac Cycle: Implications for Three-Dimensional Reconstruction and Measurements of Coronary Dimensions", Am Heart Journal, vol. 138 (5 Pt 1), pp. 865-872. 1999—Abstract Only.
Talou, Gonzalo D. Maso et al "Registration Methods for IVUS: Transversal and Longitudinal Transducer Motion Compensation", IEEE Transactions on Mbiomedical Engineering, vol. 64, No. 4, Apr. 2017.
Bredno, Jorg et al "Algorithmic Solutions for Live Device-to-Vessel Match". In Proceedings of SPIE—vol. 5370—Medical Imaging 2004: Image Processing, May 2004, pp. 1486-1497. Abstract Only.
Auvray, Vincent et al "Improved vessel enhancement for fully automatic coronary modelling". SPIE Medical Imaging 2009. Abstract Only.
Talou, Gonzalo Daniel Masa "From medical image processing to in-vivo mechanical characterization: A framework based on IVUS studies", Mar. 2017.
Barajas, Joel et al. "Cardiac Phase Extraction in IVUS Sequences using 1-D Gabor Filters", Proceedings of the 29th Annual International Conf. of the IEEE EMBX , 2007.
Matsumoto, Monica et al "Cardiac Phase Detection in Intravascular Ultrasound Images", Proceedings of SPIE, vol. 6920, pp. 1-9, 2008.

* cited by examiner

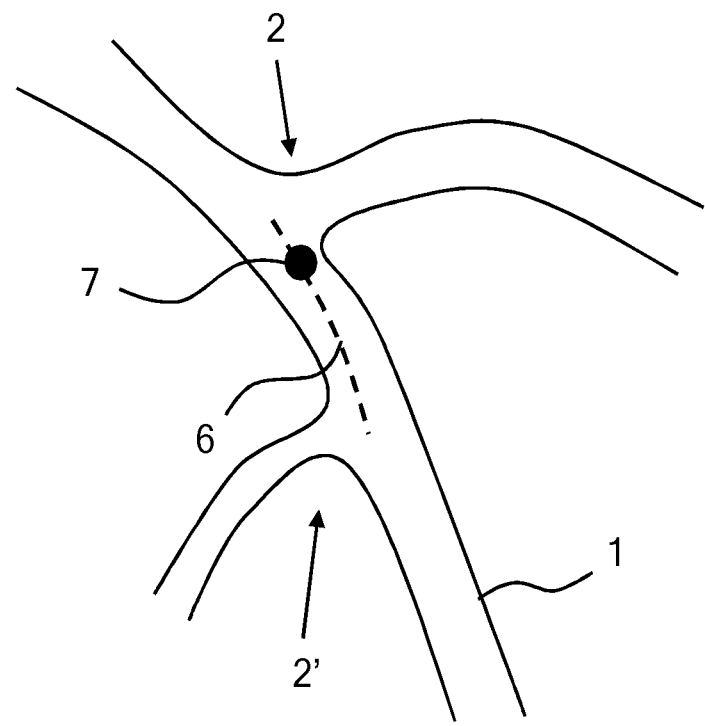
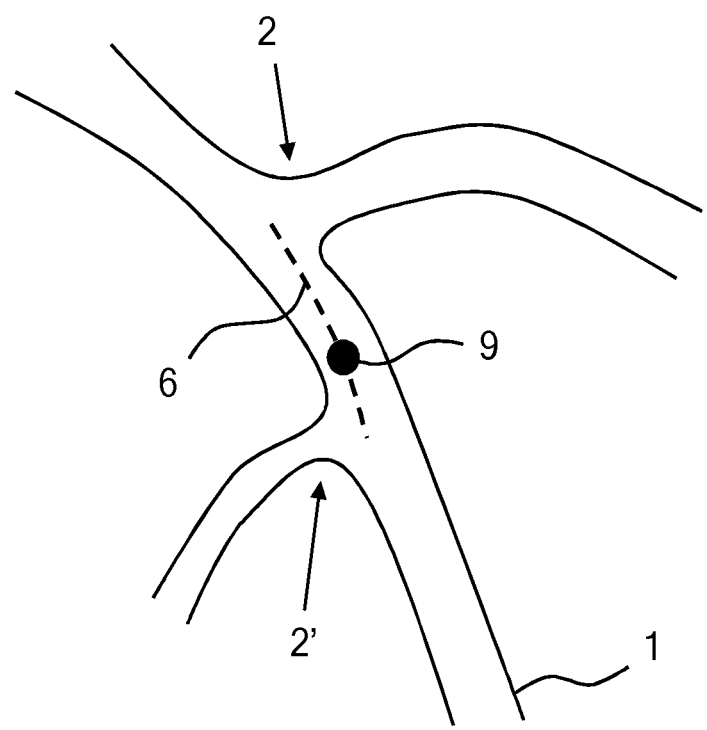
FIG. 11

INTRAVASCULAR ULTRASOUND IMAGING

CROSS-REFERENCE TO PRIOR APPLICATIONS

This application is the U.S. National Phase application under 35 U.S.C. § 371 of International Application No. PCT/EP2019/075873, filed on Sep. 25, 2019, which claims the benefit of European Patent Application No. 18290108.2, filed on Sep. 26, 2018. These applications are hereby incorporated by reference herein.

FIELD OF THE INVENTION

The present invention relates to an image processing apparatus comprising a processor arrangement adapted to receive image data including a temporal sequence of intravascular ultrasound (IVUS) images corresponding to different phases of at least one cardiac cycle, at least some of said intravascular ultrasound images corresponding to different intravascular locations.

The present invention further relates to a computer-implemented method of processing such image data including a temporal sequence of intravascular ultrasound images.

The present invention yet further relates to a computer program product for implementing such a method on a processor arrangement of an image processing apparatus.

BACKGROUND OF THE INVENTION

IVUS imaging is a valuable technique to obtain internal images of the cardiovascular system of a patient, such as the patient's arteries or heart. The IVUS images may assist in assessing a condition of the cardiovascular system, such as for example in detecting and quantifying the size of a stenosis, build-up of plaque as well as in assisting with the positioning of a medical implant such as a stent.

In order to obtain the IVUS images, a minimally invasive medical device such as a catheter or guidewire fitted with an ultrasound probe, e.g. at its tip, is inserted into the cardiovascular system of the patient, typically into an artery, after which the IVUS images are captured at regular intervals whilst slowly pulling back the minimally invasive medical device. In this manner, captured cross-sectional IVUS images of the cardiovascular system can assist in providing valuable insights into the condition of the length of the cardiovascular system imaged in this manner.

A temporal sequence 15 of such IVUS images 150 is schematically depicted in FIG. 1, here depicted by way of non-limiting example as a sequence of four IVUS images 150 captured at regular intervals denoted by capture times $T=T_0$, $T=T_1$, $T=T_2$ and $T=T_n$ respectively. Each IVUS image 150 may capture a cross-sectional view of part 1 of the cardiovascular system of a patient, e.g. an artery or the like. An anomaly 3 such as the build-up of plaque or a stenosis for example may be visible in the cross-sectional IVUS image of the part 1 of the cardiovascular system, and the IVUS image may allow for the characteristics of the anomaly 3 to be evaluated. The temporal capture frequency of the IVUS images is typically several Hz, e.g. in a range of 5-50 Hz, such that during a single cardiac cycle of the patient's heart (i.e. a single heartbeat) the temporal sequence 15 comprises a plurality of IVUS images that are captured during different phases of the cardiac cycle. This is more commonly referred to as an ungated sequence of IVUS images.

In theory, such a high density of IVUS images of the part 1 of the cardiovascular system should allow for a 3-D reconstruction of the part 1 with high longitudinal resolution in addition to the in-plane resolution of the IVUS images, especially when the pullback speed of the minimally invasive medical device is low, e.g. below 1 mm/s. However, in practice, the minimally invasive device is also displaced relative to the patient's cardiovascular system as a function of the phase of the cardiac cycle. For instance, during diastole this displacement is negligible and the overall motion of the minimally invasive medical device is dominated by its pullback speed leading to a well-defined motion in a well-defined direction. In contrast, during systole the displacement of minimally invasive medical device relative to the patient's cardiovascular system also comprises a component caused by the patient's cardiac cycle, leading to an unknown displacement of the minimally invasive medical device in an unknown direction. At present, the cause of such cardiac cycle-induced displacements of the minimally invasive device in addition to the displacement induced by the device pull-back is not fully understood. Without wishing to be bound by theory, such displacements may be caused by changes in the geometry of the patient's cardiovascular system, the blood flow through the patient's cardiovascular system or a combination of such potential causes.

Consequently, the order of the IVUS images 150 in the temporal sequence 15 does not equate to a spatially ordered volume of IVUS images 150. This is schematically depicted in FIG. 2, from which it can be seen that the spatial order of the IVUS images 150 along a length of the part 1 of the patient's cardiovascular system does not correspond to their temporal order as indicated by the labels $T_0$-$T_6$ in which a higher number indicates an IVUS image acquired at a later point in time. This means that the temporal order of ungated IVUS images 150 cannot be readily interpreted, as this would provide a distorted cross-sectional view of the part 1 of the patient's cardiovascular system. This is shown in the images in FIG. 3, in which the left image provides an anatomically correct longitudinal view of a synthetic stent in a synthetic blood vessel, whilst the middle image is constructed from a simulated ungated sequence of IVUS images 150.

For this reason, evaluation of such IVUS images 150 is usually performed on a gated volume of IVUS images 150, in which only IVUS images corresponding to the same phase of a cardiac cycle are grouped over a plurality of cardiac cycles. This yields an anatomically reliable image as shown in the right hand image in FIG. 3 but with considerable loss of longitudinal resolution due to the fact that IVUS images 150 at different phases of the cardiac cycle are not considered.

An example of such a gated acquisition of IVUS images is disclosed in "Accurate visualization and quantification of coronary vasculature by 3-D/4-D fusion from biplane angiography and intravascular ultrasound" by Andreas Wahle et al. in EBios 2000: Biomonitoring and Endoscopy Technologies; pages 144-155. In this article, the authors disclose a system for geometrically correct reconstruction of IVUS images by fusion with biplane angiography. Vessel cross-section and tissue characteristics are obtained from IVUS, while the 3-D locations are derived by geometrical reconstruction from the angiographic projections. ECG-based timing ensures a proper match of the image data with the chosen heart phase. The fusion is performed for each heart phase individually, thus yielding the 4-D data as a set of 3-D reconstructions. However, it is not straightforward to create such 4-D data from an ungated IVUS image sequence.

SUMMARY OF THE INVENTION

The present invention seeks to provide an image processing apparatus adapted to convert a temporal sequence of intravascular ultrasound (IVUS) images corresponding to different phases of at least one cardiac cycle into a spatially ordered sequence of these images.

The present invention further seeks to provide a computer-implemented method of converting such a temporal sequence of intravascular ultrasound images into a spatially ordered sequence of these images.

The present invention yet further seeks to provide a computer program product for implementing such a method on a processor arrangement of an image processing apparatus.

According to an aspect, there is provided an image processing apparatus comprising a processor arrangement adapted to receive image data corresponding to a region of interest of a patient's cardiovascular system, said image data comprising a temporal sequence of intravascular ultrasound images acquired at different phases of at least one cardiac cycle of said patient, said intravascular ultrasound images imaging overlapping volumes of the patient's cardiovascular system and implement a spatial reordering process of said temporal sequence of intravascular ultrasound images by evaluating the image data to select at least one spatial reference associated with said temporal sequence of intravascular ultrasound images; estimating a distance to the at least one spatial reference for each of the intravascular ultrasound images of said temporal sequence; and reordering said temporal sequence of intravascular ultrasound images into a spatial sequence of intravascular ultrasound images based on the estimated distances; and generate an output comprising said spatial sequence of intravascular ultrasound images.

Such a spatially reordered sequence of IVUS images can be used to generate a high resolution and low-distortion visualization of the region of interest of the cardiovascular system of the patient, such as of a coronary artery. In particular, at least some embodiments of the present invention leverage the characteristic that the depth of view of each intravascular ultrasound image is large compared to the displacement (pullback) speed of the invasive medical device, such that a large overlap in imaged volumes of the patient's cardiovascular system is present between different intravascular ultrasound images of this sequence. This for example allows for a first order approximation of each intravascular ultrasound image of the sequence imaging the same volume of the patient's cardiovascular system, which allows for spatial displacement of the intravascular ultrasound images relative to each other to be estimated using motion estimation algorithms.

For example, in a first main embodiment of this invention, the temporal sequence of intravascular ultrasound images covers a plurality of cardiac cycles, and wherein the processor arrangement is further adapted, within said spatial reordering process, to evaluate the temporal sequence of intravascular ultrasound images by gating said intravascular ultrasound images into a plurality of intravascular ultrasound image groups, each group consisting of intravascular ultrasound images corresponding to approximately the same phase of the cardiac cycles; and select one of said intravascular ultrasound image groups as the spatial reference, wherein estimating the distance from the spatial reference for each of the remaining intravascular ultrasound images of said temporal sequence comprises, for each remaining intravascular ultrasound image group (Vi), estimating said distance for each intravascular ultrasound image of the remaining intravascular ultrasound image group relative to an intravascular ultrasound image in the spatial reference using a motion estimation algorithm.

The main advantage of this embodiment is that the ungated IVUS images may be spatially ordered without the need for a secondary imaging technique, such as angiography. Not only does this simplify the IVUS image processing, but it also limits the exposure of the patient to potentially harmful radiation, thereby improving the safety of a medical procedure during which the IVUS images are captured. Moreover, by bundling the IVUS images into gated groups, the insight that for a given phase of a multitude of cardiac cycles the cycle-induced displacement of a probe with which the IVUS images is unidirectional and only slowly varying, a large number of constraints may be applied to the motion estimation of the IVUS images within an IVUS image group, thereby reducing the risk of incorrect estimation of the displacement of the IVUS images within the group relative to the spatial reference. A further advantage is that the spatial reordering of the ungated sequence of IVUS images does not rely on the detection of an anatomical landmark to be used as a reference for the spatial reordering, which anatomical landmark typically needs to be provided by secondary imaging techniques such as angiographic imaging. Instead, one of the gated groups of IVUS images may be used as the spatial reference as it has been found that such a spatial reference can provide an accurate spatial reordering of the IVUS images due to the aforementioned similarity of the various IVUS images in the sequence, which allows displacement of such images relative to each other to be determined using motion estimation techniques. In fact, due to the large depth of view of the IVUS images relative to the distance between the IVUS images in the temporal sequence, the IVUS images may be treated as imaging the same anatomical landscape with a longitudinal shift between IVUS images.

In order to obtain a reliable spatial reference, it is preferable that gating errors in the acquisition of the IVUS images do not significantly affect the accuracy of this static reference. Such gating errors can occur for example where the capturing of an IVUS image at a specific phase of a cardiac cycle is difficult to achieve, for example where the heartbeat is fast. For this reason, the processor arrangement may be further adapted to select an intravascular ultrasound image group comprising intravascular ultrasound images captured during a diastolic phase of the cardiac cycles as the spatial reference, as during diastole the heart status is stable for some time spatial displacements of an IVUS image resulting from gating errors are negligible.

Alternatively, the processor arrangement may be further adapted to, for each intravascular ultrasound image group having a subsequent temporally neighboring intravascular ultrasound image group, determine a difference between each intravascular ultrasound image of the intravascular ultrasound image group and the intravascular ultrasound image of a corresponding cardiac cycle of the subsequent temporally neighboring intravascular ultrasound image group; sum the determined differences to obtain a further group difference; and select the intravascular ultrasound image group exhibiting the smallest further group difference as the spatial reference. This is another suitable approach to find a reliable spatial reference, as finding a gated IVUS image group that has a temporally neighboring group of IVUS images with minimal spatial displacement ensures that a small temporal gating error will only result in a small change (shift) in terms of captured IVUS image. This for example is a suitable alternative manner of finding a spatial reference largely insensitive to gating errors such as a diastolic spatial reference, which is advantageous where cardiac phase information is not available to the processor arrangement.

In estimating the distance for each intravascular ultrasound image of the remaining intravascular ultrasound image group relative to an intravascular ultrasound image in the spatial reference, the processor arrangement may be adapted to determine a group-level distance, i.e. a single distance that is common to all IVUS images within the remaining IVUS image group. This is a straightforward and rapid approach that yields good results where the region of interest of the patient's cardiovascular system imposes cardiac cycle-induced displacements of the invasive medical device that are largely constant across the region of interest.

However, such an approach may be refined in a scenario where such cardiac cycle-induced displacements of the invasive medical device vary across the region of interest, for example because of changes in the anatomy, e.g. narrowing or widening of a coronary artery through which the invasive medical device is displaced or the minimally invasive medical device entering a stiffer or more flexible section of the anatomy that will alter the response of the anatomy to the cardiac cycle. To this end, the motion estimation algorithm may be adapted to estimate an optimal distance for each intravascular ultrasound image of the remaining intravascular ultrasound image group relative to an intravascular ultrasound image in the spatial reference, i.e. the displacement distance for each IVUS image in the remaining IVUS image group is individually optimized relative to an IVUS image in the spatial reference to more accurately compensate for such variations in the magnitude of the cardiac cycle-induced displacement of the invasive medical device.

As will be understood from the foregoing, the spatial position of a gated volume of IVUS images, i.e. an IVUS image group, is determined by translating the IVUS image group along a translation coordinate or a plurality of translation coordinates in case of individually optimized translations for the respective IVUS images of the group as explained above, which typically corresponds to or approximates the translation coordinate of the invasive medical device used to capture the IVUS images, and by utilizing a similarity between the translated IVUS images within an IVUS image group under investigation and the IVUS images within the spatial reference, i.e. the reference IVUS image group.

The accuracy of this approach may be further improved in that the processor arrangement may be further adapted to estimate the intravascular distance from the spatial reference for each of the remaining intravascular ultrasound image groups of said temporal sequence by identifying a spatially neighboring intravascular ultrasound image group to the spatial reference; augmenting the spatial reference by merging the spatially neighboring intravascular ultrasound image group with the spatial reference and spatially repositioning the intravascular ultrasound images of the augmented spatial reference. Such an augmentation operation allows for the resolution of the spatial reference to be improved. Although in principle such improvement of the resolution may be achieved using any of the spatially repositioned IVUS image groups, as there is an increased risk that the repositioning of a systolic IVUS image group is less accurate in the presence of gating errors within the group for instance, it is preferred that such an augmentation operation is performed using a spatially neighboring IVUS image group, e.g. an IVUS image group corresponding to a neighboring cardiac phase.

In a further embodiment, once the temporal sequence of IVUS images has been spatially reordered as per the above described embodiments, the processor arrangement may be adapted to repeat the spatial reordering process. This typically involves gating the spatially reordered temporal sequence of IVUS images into a plurality of gated IVUS image groups and repeating the selection of a spatial reference and estimating the displacement of the remaining gated IVUS image groups relative to the spatial reference followed by the spatial reordering based on the thus estimated distances to further improve the spatial reordering of the temporal sequence of IVUS images. The processor arrangement may be adapted to repeat this spatial reordering process several times, e.g. in an iterative manner in which the process is terminated once a fixed number of iterations has been performed or the spatial reordering no longer changes the determined spatial location of the IVUS images of the temporal sequence.

To further improve the accuracy of the spatial reordering operation performed on the temporal sequence of the IVUS images, the processor arrangement may be further adapted to apply a 2D lateral motion compensation algorithm to the intravascular ultrasound images of said temporal sequence prior to gating the intravascular ultrasound images into a plurality of intravascular ultrasound image groups. Such (2-D) motion compensation may compensate for lateral motions in the cardiovascular region of interest present in the temporal sequence of IVUS images, e.g. lateral motions introduced by the pullback, such that the only remaining predominant motion is the longitudinal motion corresponding to the pullback direction of the invasive medical device.

In accordance with another main embodiment of the present invention, said image data further comprises a temporal sequence of fluoroscopic images of said region of interest captured under a viewing angle in which an invasive medical device used to capture the temporal sequence of intravascular ultrasound images is visible, wherein each fluoroscopic image is captured at the same time of the at least one cardiac cycle as a corresponding intravascular ultrasound image of the temporal sequence of intravascular ultrasound images; and a separately recorded temporal sequence of angiographic images of said patient region of interest captured under said viewing angle, wherein each angiographic image is captured at approximately the same phase of the at least one cardiac cycle as a corresponding fluoroscopic image of the temporal sequence of fluoroscopic images; wherein the processor arrangement is further adapted to temporally register each intravascular ultrasound image of the temporal sequence of intravascular ultrasound images to a fluoroscopic image of the temporal sequence of fluoroscopic images; temporally register each fluoroscopic image of the temporal sequence of fluoroscopic images to an angiographic image of the temporal sequence of angiographic images; identify the invasive medical device in said fluoroscopic images; extract a path of the identified invasive medical device through the patient's cardiovascular system relative to the registered fluoroscopic and angiographic images; identify a set of anatomical landmarks from the angiographic images of the temporal sequence of angiographic images that are common to said angiographic images; divide the extracted path of the identified invasive medical device through the patient's cardiovascular system into a plurality of path segments, each defining a spatial reference, wherein each path segment is bound by a neighboring pair of said anatomical landmarks and at least in part reorder said temporal sequence of intravascular ultrasound images into a spatial sequence of intravascular ultrasound images based on the distance of an intravascular ultrasound probe from said temporal sequence along a path segment to one of the anatomical landmarks binding said path segment. This ensures that the IVUS images can be correctly spatially reordered, even where large changes in the geometry of the region of interest of the patient's cardiovascular system caused by the phase changes in the patient's cardiac cycle are present. This is because the anatomical landmarks behave as stable anchors in the image data, which therefore can be relied upon irrespective of the actual geometry of the region of interest. In other words, even though the 2-D projections of the regions of interest of the patient's cardiovascular system can drastically change shape during the patient's cardiac cycle, the relative positions of the anatomical landmarks over the segments remain intact and can therefore be relied upon. Hence, with such a co-registration approach, a progressive and monotonic sampling of the region of interest of the patient's cardiovascular system is achieved.

The position of the invasive medical device through the patient's cardiovascular system relative to the registered fluoroscopic and angiographic images may be identified in any suitable manner, such as from the registered fluoroscopic and angiographic images or alternatively by leveraging its distance from a device such as an injection catheter from which it extends. Other suitable co-registration techniques for co-registering the minimally invasive medical device with the registered fluoroscopic and angiographic images will be apparent to the skilled person.

In a specific embodiment, the processor arrangement is further adapted to spatially and temporally register each fluoroscopic image of the temporal sequence of fluoroscopic images to an angiographic image of the temporal sequence of angiographic image using a cardiac road mapping algorithm, which is a straightforward approach to such a registration process.

The processor arrangement may be further adapted to extract the path of the invasive medical device through the patient's cardiovascular system from the registered fluoroscopic and angiographic images by extracting a centreline of said path through the patient's cardiovascular system. In this manner, the path of the invasive medical device through the patient's cardiovascular system can be determined by a high degree of accuracy.

According to another aspect, there is provided a computer-implemented method of processing a temporal sequence of intravascular ultrasound images corresponding to different phases of at least one cardiac cycle, the method comprising receiving image data corresponding to a region of interest of a patient's cardiovascular system, said image data comprising said temporal sequence of intravascular ultrasound images, said intravascular ultrasound images imaging overlapping volumes of the patient's cardiovascular system; implementing a spatial reordering process of said temporal sequence of intravascular ultrasound images by evaluating the image data to select at least one spatial reference associated with said temporal sequence of intravascular ultrasound images; estimating a distance to the at least one spatial reference for each of the intravascular ultrasound images of said temporal sequence; and reordering said temporal sequence of intravascular ultrasound images into a spatial sequence of intravascular ultrasound images based on the estimated distances; and generating an output comprising said spatial sequence of intravascular ultrasound images.

With such a method, an ungated temporal sequence of IVUS images may be readily reordered into a spatial sequence such that an anatomically reliable 3-D representation of a region of interest of a patient's cardiovascular system can be generated.

In a first embodiment, the temporal sequence of intravascular ultrasound images covers a plurality of cardiac cycles, and the method further comprises, within said spatial reordering process, evaluating the temporal sequence of intravascular ultrasound images by gating said intravascular ultrasound images into a plurality of intravascular ultrasound image groups, each group consisting of intravascular ultrasound images corresponding to approximately the same phase of the cardiac cycles; and selecting one of said intravascular ultrasound image groups as the spatial reference; wherein estimating the distance from the spatial reference for each of the remaining intravascular ultrasound images of said temporal sequence comprises, for each remaining intravascular ultrasound image group (Vi), estimate said distance for each intravascular ultrasound image of the remaining intravascular ultrasound image group relative to an intravascular ultrasound image in the spatial reference using a motion estimation algorithm. This amongst other advantages as explained above facilitates a spatial reordering of the temporal sequence of IVUS images without the need to locate an anatomical landmark within the region of interest of a patient's cardiovascular system, as this typically requires a secondary sequence of images, e.g. angiographic images, in which such an anatomical landmark can be identified.

In a second embodiment, the image data further comprises a temporal sequence of fluoroscopic images of said region of interest captured under a viewing angle in which an invasive medical device used to capture the temporal sequence of intravascular ultrasound images is visible, wherein each fluoroscopic image is captured at the same time of the at least one cardiac cycle as a corresponding intravascular ultrasound image of the temporal sequence of intravascular ultrasound images; and a separately recorded temporal sequence of angiographic images of said patient region of interest captured under said viewing angle, wherein each angiographic image is captured at approximately the same phase of the at least one cardiac cycle as a corresponding fluoroscopic image of the temporal sequence of fluoroscopic images; the method further comprising temporally registering each intravascular ultrasound image of the temporal sequence of intravascular ultrasound images to a fluoroscopic image of the temporal sequence of fluoroscopic images; temporally registering each fluoroscopic image of the temporal sequence of fluoroscopic images to an angiographic image of the temporal sequence of angiographic images; identifying the invasive medical device in said fluoroscopic images, extracting a path of the identified invasive medical device through the patient's cardiovascular system from the registered fluoroscopic and angiographic images; identifying a set of anatomical landmarks from the angiographic images of the temporal sequence of angiographic images that are common to said angiographic images; dividing the extracted path of the identified invasive medical device through the patient's cardiovascular system into a plurality of path segments, each defining a spatial reference, wherein each path segment is bound by a neighboring pair of said anatomical landmarks and at least in part reordering said temporal sequence of intravascular ultrasound images into a spatial sequence of intravascular ultrasound images based on the distance of an intravascular ultrasound image from said temporal sequence along a path segment to at least one of the anatomical landmarks binding said path segment. With such a co-registration method, a progressive and monotonic sampling of the region of interest of the patient's cardiovascular system is achieved.

According to yet another aspect, there is provided a program product computer program product comprising a computer readable storage medium having computer readable program instructions embodied therewith for, when executed on a processor arrangement of an image processing apparatus, cause the processor arrangement to implement the method of any of the herein described embodiments. Such a computer program product for example may be used to upgrade or otherwise alter existing image processing apparatuses, thereby avoiding the need for a more costly replacement of such existing image processing apparatuses with new devices adapted to implement such a method.

BRIEF DESCRIPTION OF THE DRAWINGS

Embodiments of the invention are described in more detail and by way of non-limiting examples with reference to the accompanying drawings, wherein:

FIG. 11 schematically depict an aspect of this method.

DETAILED DESCRIPTION OF THE EMBODIMENTS

Figure 1:
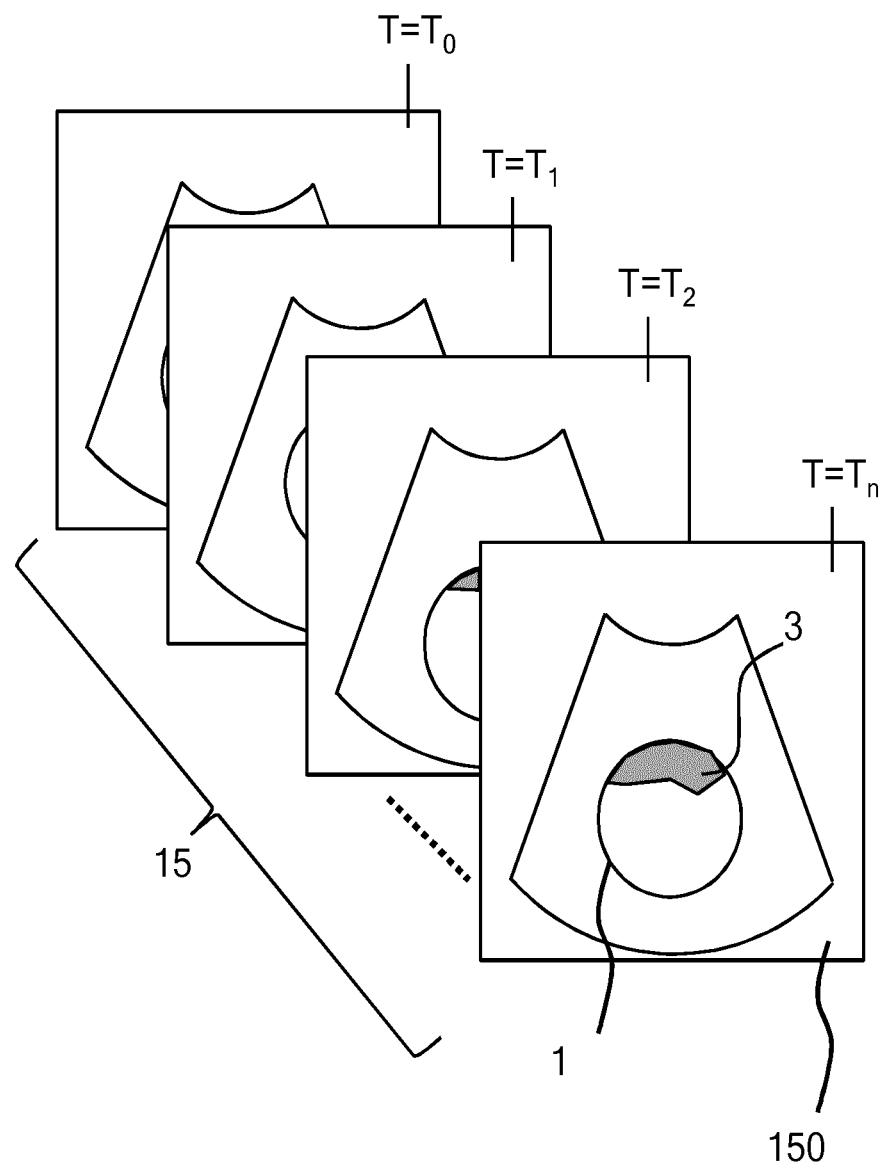
FIG. 1 schematically depicts a temporal sequence of IVUS images.
Figure 2:
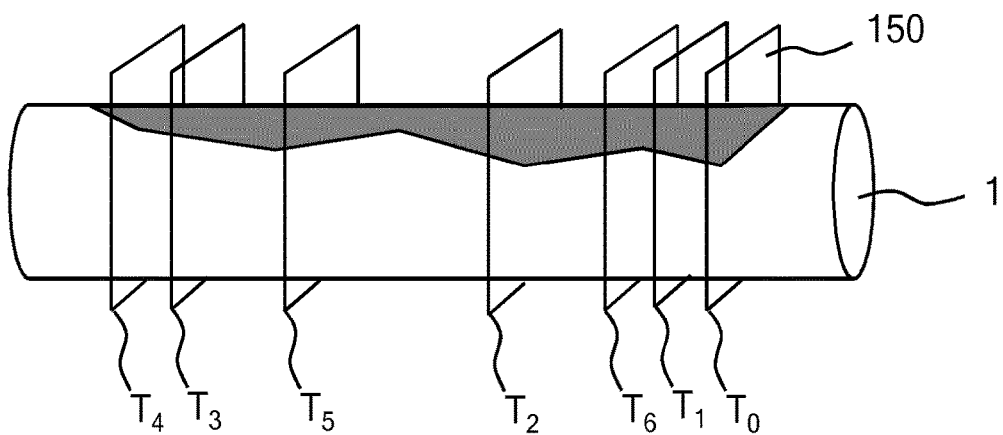
FIG. 2 schematically depicts a spatial distribution of a temporal sequence of IVUS images along a section of a cardiovascular system of a patient.

It should be understood that the Figures are merely schematic and are not drawn to scale. It should also be understood that the same reference numerals are used throughout the Figures to indicate the same or similar parts.

Figure 4:
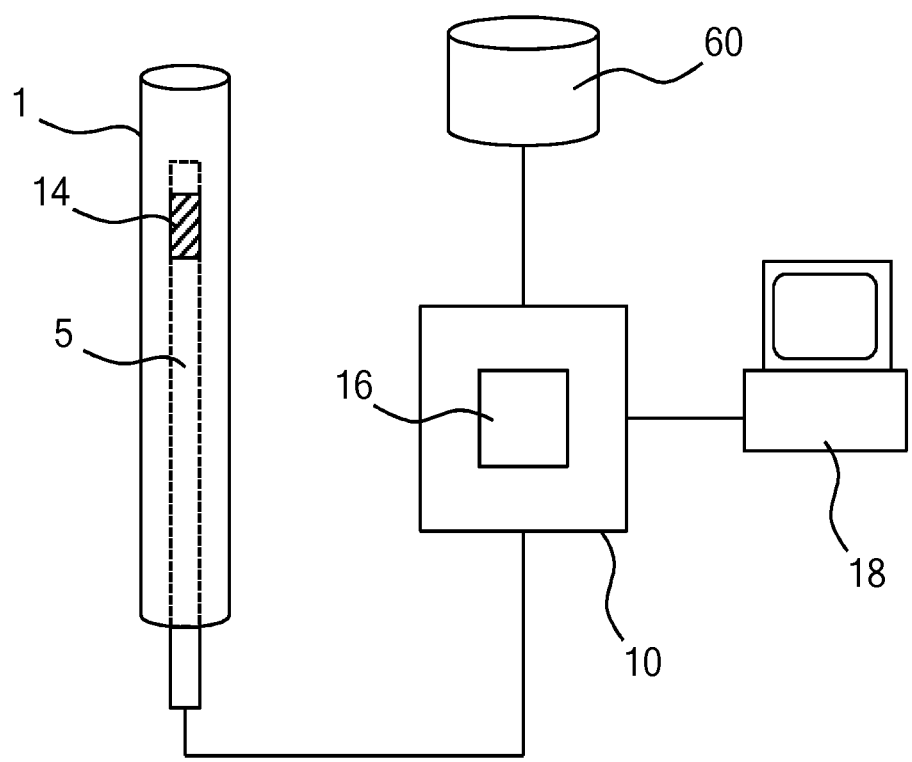
FIG. 4 schematically depicts an IVUS imaging system according to an example embodiment.

FIG. 4 shows a schematic illustration of an IVUS imaging system 100, in particular a two-dimensional (2D) IVUS imaging system or three-dimensional (3D) IVUS imaging system. The IVUS imaging system 100 may be applied to intravascularly inspect a region of interest 1 of a cardiovascular system of a patient such as for example a section of an artery, e.g. the coronary artery, peripheral arteries, and so on. The IVUS imaging system 100 comprises an invasive medical device 5, e.g. a catheter or guidewire, including an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements may be arranged in a linear array in case of a 2D IVUS imaging system 100 or may be arranged in a two-dimensional array, in particular for providing a multi-planar or three-dimensional image in case of a 3D IVUS imaging system 100. The ultrasound probe 14 may be mounted in any suitable location on the invasive medical device 5, e.g. on or proximal to the tip of the invasive medical device 5.

Further, the IVUS imaging system 100 comprises an image processing apparatus 10 including a processor arrangement 16 that controls the provision of a 2D or 3D image sequence via the IVUS imaging system 100. As will be explained in further detail below, the processor arrangement 16 may control not only the acquisition of data via the transducer array of the ultrasound probe 14, but also signal and image processing that form the 2D or 3D IVUS image sequence out of the echoes of the ultrasound beams received by the transducer array of the ultrasound probe 14. In addition, the processor arrangement is responsible for spatially reordering a temporal sequence 15 of IVUS images 150 into a spatially ordered sequence of IVUS images 150 in accordance with embodiments of the present invention, as will be explained in more detail below.

The IVUS imaging system 100 may further comprise a display device 18 (from here on also referred to as display 18) for displaying the (spatially reordered) 2D or 3D image sequence to the user. Still further, an input device 20 may be provided that may comprise keys or a keyboard 22 and further inputting devices, for example a trackball 24. The input device 20 might be connected to the display 18 or directly to the processor arrangement 16.

The ultrasound system 100 may further comprise a data storage arrangement 60, e.g. one or more memory devices, hard disks, optical discs, or the like, in which the processor arrangement 16 may store image frames, e.g. the temporal sequence of IVUS images and/or the spatially reordered sequence of IVUS images for evaluation at a later date.

Figure 5:
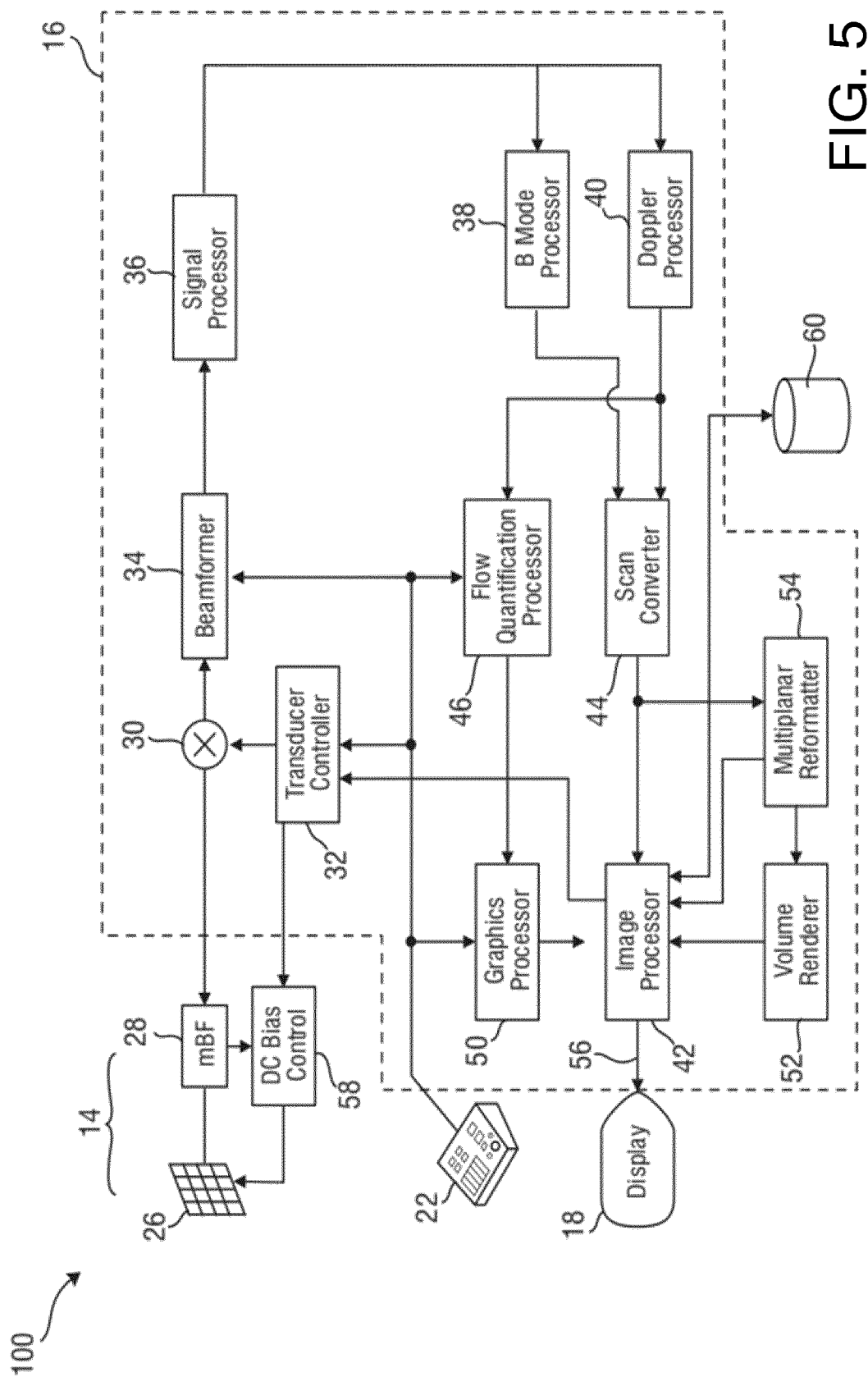
FIG. 5 schematically depicts an IVUS imaging system according to an example embodiment in block diagram form.

FIG. 5 illustrates a schematic block diagram of an IVUS imaging system 100 including a processor arrangement 16 of the image processing apparatus 10 adapted to process intravascular ultrasound (IVUS) images obtained from an ultrasound probe 14 on an invasive medical device 5 for intravascular investigation, such as a catheter or guide wire. The ultrasound probe 14 may, for example, comprise a CMUT transducer array 26. The transducer array 26 may alternatively comprise piezoelectric transducer elements formed of materials such as PZT or PVDF.

The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable or probe wires, which may be integral to the invasive medical device, to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the CMUT array. The DC bias control 58 sets DC bias voltage(s) that are applied to the CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part of the processor arrangement 16 of the image processing apparatus 10 according to embodiments of the present invention. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40, which may also form part of the processor arrangement 16 of the image processing apparatus 10 according to embodiments of the present invention. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field.

In a 3D imaging system, the multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3D image sequence 56 is transferred from the scan converter 44, multiplanar reformatter 54, and volume renderer 52 to an image processor 42 for further enhancement, buffering and temporary storage for display on the display 18.

In addition to being used for imaging, the blood flow values produced by the Doppler processor 40 and tissue structure information produced by the B mode processor 38 may be transferred to a quantification processor 46 forming part of the processor arrangement 16. This quantification processor 46 may produce measures of different flow conditions such as the volume rate of blood flow as well as structural measurements such as the dimensions of anatomical anomalies within the vascular system of a patient, such as a stenosis, build-up of plaque within the patient's arteries, and so on. The quantification processor 46 may receive input from the user control panel 22, such as the point in the anatomy of an image where a measurement is to be made.

Output data from the quantification processor 46 may be transferred to a graphics processor 50 forming part of the processor arrangement 16 for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images in case of a 3D imaging system.

Again, it shall be noted that the aforementioned IVUS imaging system 100 has only been explained as one possible example for an application of the image processing device 10. It shall be noted that the aforementioned IVUS imaging system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 5.

As explained in more detail above, in order to recreate an undistorted 3-D image of a region of interest 1 of the cardiovascular system of a patient from a temporal sequence 15 of IVUS images 150, it is necessary to spatially reorder the temporal sequence 15 of IVUS images 150 in order to compensate for displacement of the ultrasound probe 14 on the invasive medical instrument 5 during certain phases of the cardiac cycle as without such compensation the IVUS images 150 appear to jump back and forth within the cardiovascular system of the patient when visualizing the region of interest 1 based on the temporal sequence 15.

Figure 6:
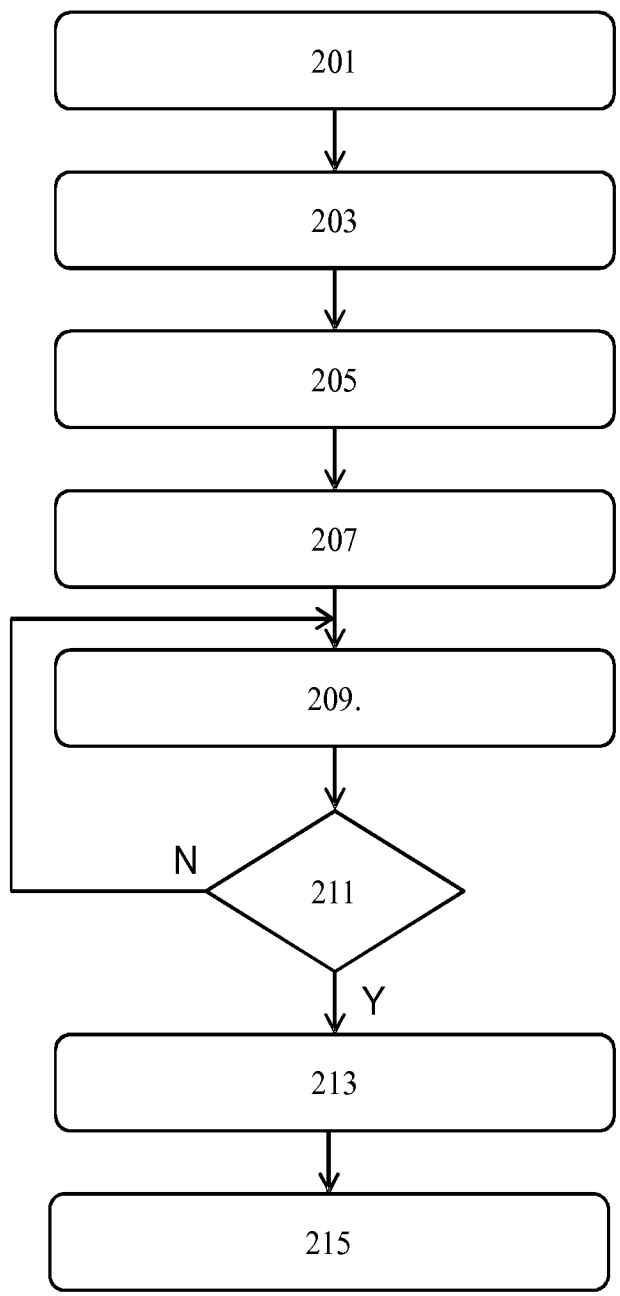
FIG. 6 is a flowchart of a method implemented by a processor arrangement of an image processing apparatus according to an embodiment.

In a first main embodiment, the processor arrangement 16 of the image processing apparatus 10 is adapted to implement the method 200 in order to achieve such spatial reordering, a flow chart of which method is shown in FIG. 6. At this point, it is noted that the processor arrangement 16 may be adapted to implement the methods 200 and/or 300 entirely in software by executing computer program instructions that are loaded onto the processor arrangement 16. Alternatively, the processor arrangement 16 may be adapted to implement the method 200 and/or 300 partially in software and partially in hardware, to which end the processor arrangement 16 may comprise one or more processing units, e.g. application-specific integrated circuits, which are hard-coded to implement certain aspects of the method 200 and/or 300. As a further alternative, the processor arrangement 16 may be adapted to implement the method 200 and/or 300 entirely in hardware.

In operation 201, the processor arrangement 16 is adapted to receive a temporal sequence 15 of IVUS images 150. The temporal sequence 15 may be a live sequence that is obtained directly from an ultrasound probe 14 of an invasive medical device 5 such as a catheter or guide wire or alternatively the processor arrangement 16 may receive the temporal sequence 15 as a previously stored sequence of IVUS images 150 from the data storage device 60. The latter scenario facilitates post-procedural evaluation of the IVUS images 150, for instance in scenarios in which the appropriate medical practitioner is not present during a procedure in which the IVUS images 150 are captured.

The processor arrangement 16 may be further adapted in some embodiments to perform operation 203 in which the IVUS images 150 are pre-processed. Such pre-processing for example may be desirable where at least some of the images exhibit cardiac cycle-induced (2-D) lateral motions in the acquisition plane in addition to the longitudinal motions along a length of the region of interest 1 that the processor arrangement 16 seeks to compensate for. It therefore may be desirable to compensate for such 2-D lateral motions prior to the longitudinal motion compensation of the IVUS images 150 to make the subsequent longitudinal motion compensation as straightforward as possible. A straightforward approach to such lateral motion compensation is to compensate for the motion between successive pairs of IVUS images 150. Many suitable 2-D motion estimation methods such as block matching, spline-based motion estimation, parametric motion estimation, diffeomorphic motion estimation and so on may be used for such lateral motion compensation. As such techniques are well-known per se to the skilled person, they are not explained in any further detail here for the sake of brevity only. However, it should be understood from the foregoing that operation 203 is entirely optional and may be omitted from the method 200 without departing from the teachings of the present application.

In operation 205, the processor arrangement 16 is adapted to gate the sequence 15 of IVUS images 150 into a plurality of groups or volumes of IVUS images 150, wherein within each group or volume the IVUS images 150 correspond to the same phase of different cardiac cycles. In order to determine the relationship between an IVUS image 150 and the phase of the cardiac cycle of the patient, a number of techniques may be deployed. For example, in case the pullback of the invasive medical device 5 is accompanied by the acquisition of an ECG of the patient, the heart phase may be inferred by interpolation from periodic features within the ECG, such as QRS peaks.

Alternatively, the phase of the cardiac cycle may be derived from the IVUS images 150 themselves, as for instance suggested by Aura Hernandez et al., in "Image-based ECG sampling of IVUS sequences", 2008 IEEE Ultrasonics Symposium, ISBN 978-1-4244-2428-3. Such phase determination methods typically rely on the extraction of some periodically varying indicators from the IVUS images 150, such as for example correlation between successive images, estimated lateral motion amplitude of an IVUS image 150 (which may be determined in operation 203 as well), sum of the gradients in the IVUS images 150, and so on, which periodic variations are indicative of a particular phase of the cardiac cycle.

The processor arrangement 16 next proceeds to operation 207 in which the processor arrangement is adapted to select a reference group or volume from the plurality of groups or volumes of gated IVUS images 150. This reference will be used to reposition the remaining groups or volumes of gated IVUS images 150 relative to the selected reference in order to achieve the spatial reordering of the temporal sequence 15 of IVUS images 150. In a theoretical situation in which the cardiac phase associated with the IVUS images 150 would be perfectly defined, the selection of this spatial reference would be arbitrary. However, in reality gating errors will be present in the groups of gated IVUS images 150. Typically this error can be up to 5-10%; for example, where 20 to 30 IVUS images 150 are captured during a single cardiac cycle, the gating errors in such a group or volume may cause the IVUS images 150 within such a group to be 1 or 2 phases off the correct phase.

Such a gating error is largely without consequence where the patient's heart is at rest such as during diastole, as in such a scenario the gating error is not associated with a considerable longitudinal displacement of the ultrasound probe 14. However, during systole, the patient's heart is moving fast such that between successive IVUS images 150 a large longitudinal displacement may have taken place, e.g. of up to 1 mm. Moreover, the magnitude of such a cardiac-induced longitudinal motion can largely vary depending on the geometry of the section of the cardiovascular system in which the ultrasound probe 14 is present, which can lead to unpredictable errors within the spatial reference if this reference corresponds to a phase of the cardiac cycle during systole. It is therefore desirable to select a group of gated IVUS images 150 as the spatial reference for which any gating errors present within the group do not affect the accuracy or reliability of the spatial reference. An acceptable spatial reference for example is a group of gated IVUS images 150 corresponding to a cardiac phase associated with diastole of the heart during which the heart is at rest as previously explained.

The selection of such a spatial reference may be based on available ECG data as previously mentioned. Alternatively, in the absence of such ECG data, the selection of such a spatial reference may be obtained by the processor arrangement 16 being arranged to determine a difference between each IVUS image 150 of an IVUS image group and the IVUS image 150 of a corresponding cardiac cycle of the subsequent temporally neighboring IVUS image group by subtracting the two images from each other. As will be understood from the foregoing, where the two temporally neighboring IVUS images 150 that are subtracted from each other correspond to a diastolic phase of the cardiac cycle, their difference will be small, i.e. the subtraction result will be small, whereas for the relatively large displacements of the ultrasound probe 14 during systole, the difference (subtraction result) between such temporally neighboring IVUS images 150 will be much larger, even when ignoring the effect of potential gating errors. Upon completing the subtraction operation for all temporally neighboring IVUS images 150 in the two groups, the processor arrangement 16 sums the determined differences to obtain a group difference. In this manner, a group difference is determined for all temporally neighboring IVUS image groups after which the processor arrangement 16 selects the intravascular ultrasound image group exhibiting the smallest group difference as the spatial reference in order to obtain a stable and reliable spatial reference.

The processor arrangement 16 is further adapted to subsequently perform operation 209 in which the processor arrangement 16 estimates the intravascular distance between the spatial reference and each of the remaining groups of gated IVUS images 150 for each of the remaining IVUS images of said temporal sequence. This may be achieved using readily available motion estimation algorithms. This is because each IVUS image images a particular volume of the patient's cardiovascular system, in which the depth of view of the IVUS image is typically much larger than the displacement between neighboring IVUS images in the temporal sequence, or even between IVUS image groups. In other words, a large overlap in imaged subject matter exists between the IVUS images of such IVUS image groups, which may be leveraged by motion estimation techniques to estimate the displacement of one IVUS image relative to another. This is explained in more detail with the aid of FIG. 7 and FIG. 8 in which two groups or volumes of gated IVUS images 150 are schematically depicted; the spatial reference volume $V_{ref}$ and the selected volume $V_i$ that is to be spatially matched to the reference volume $V_{ref}$. The task of the motion estimation algorithm is to find the displacement of the selected volume $V_i$ relative to the spatial reference $V_{ref}$, i.e. the distance between $V_i$ and $V_{ref}$. This may be achieved by identifying communalities 155 between the IVUS images 150 in the selected volume $V_i$ relative to the spatial reference $V_{ref}$ and mapping these communalities 155 onto each other, e.g. by spatially displacing the selected IVUS image group $V_i$ relative to the spatial reference $V_{ref}$ and determining for which displacement optimal matching of these communalities 155 is achieved. This displacement equates to the distance between the selected volume $V_i$ and the spatial reference $V_{ref}$.

Figure 7:
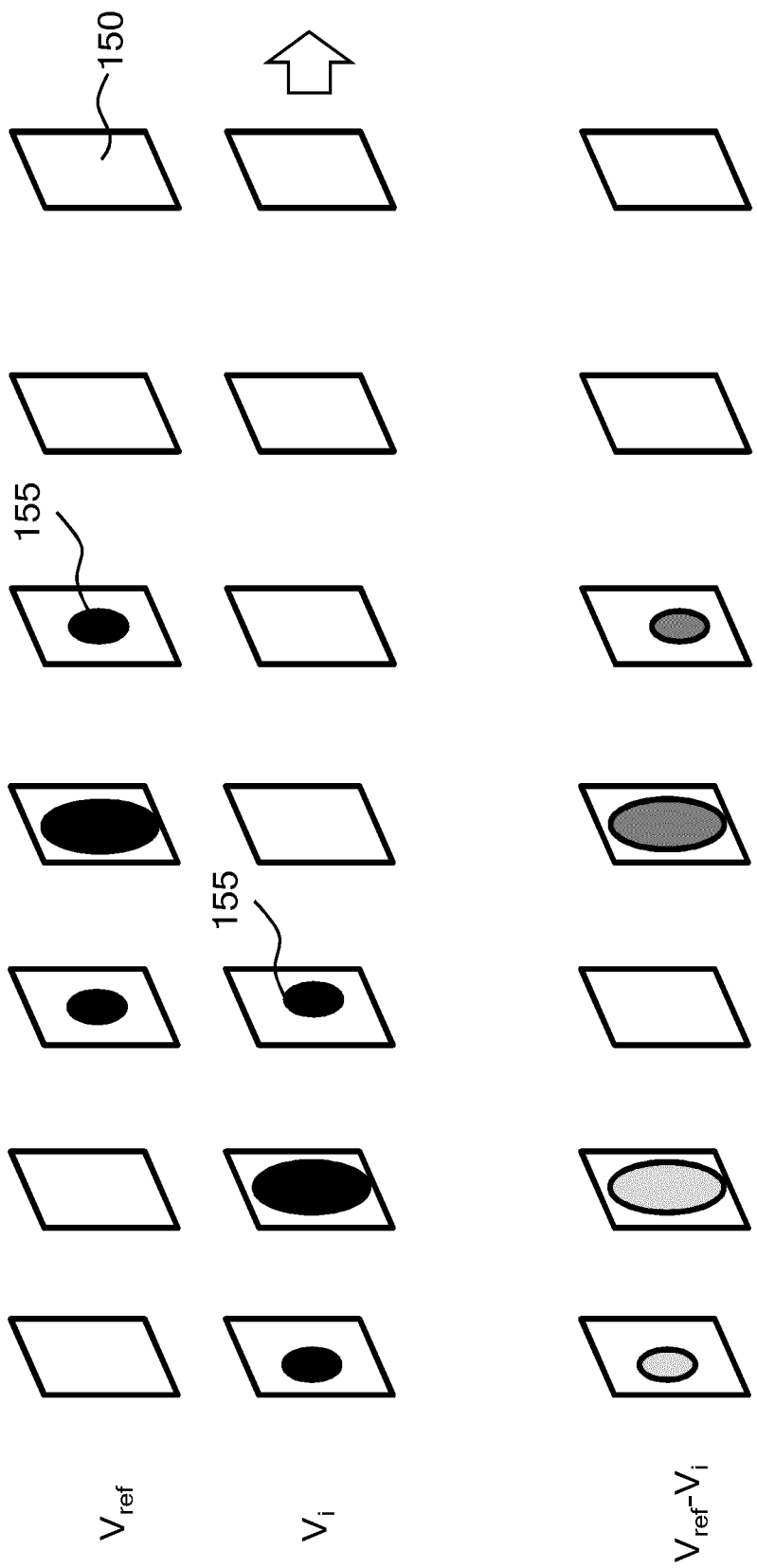
FIG. 7 and FIG. 8 schematically depict aspects of this method.
Figure 8:
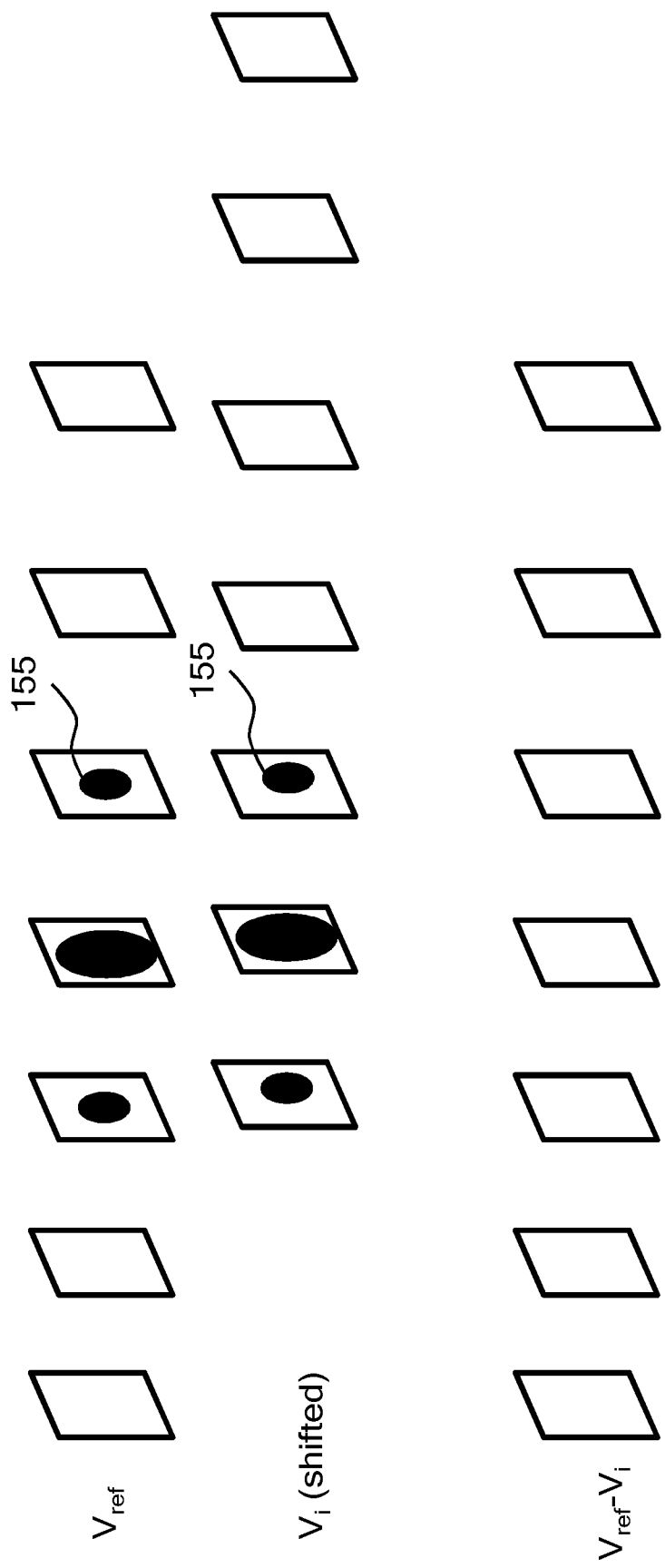

FIG. 7 schematically depicts the comparison between the spatial reference $V_{ref}$ and a selected group of gated IVUS images 150 without longitudinal displacement of the selected group in which the bottom series depicts the difference ($V_{ref}-V_i$) between the individual images of the spatial reference and the selected group of gated IVUS images 150 (dark grey highlights a positive difference value and light grey highlights a negative difference value). In FIG. 8 the selected group of gated IVUS images 150 is longitudinally displaced in the direction of the block arrow in FIG. 7. This longitudinal displacement may be performed in a stepwise fashion and for each step the group difference value between the spatial reference and the selected group of gated IVUS images 150 is determined as described above. From these the determined differences, the processor arrangement 16 selects the longitudinal displacement value for which this group difference is minimal as an estimate of the longitudinal displacement of the selected group of gated IVUS images 150 relative to the spatial reference. However, it will be understood by the skilled person that the motion estimation algorithm is not limited to determining the difference between such IVUS image groups but instead may deploy any suitable function or metric to determine the quality of the alignment of these IVUS image groups. Moreover, the skilled person further knows that the displacement between groups can be modelled with motion models of different complexities, from a unique global translation to affine fields to fields decomposed over splines to dense motion fields. Finally, the skilled person may estimate the said motion field in any suitable manner known to him or her, such as by exhaustive methods, iterative methods, learning-based methods, etc.

The processor arrangement 16 checks in operation 211 if the longitudinal displacement of all groups of gated IVUS images 150 relative to the spatial reference has been determined. If this is not the case, the processor arrangement returns to operation 209 until all longitudinal displacements have been estimated after which the processor arrangement 16 proceeds to operation 213.

In operation 213, the processor arrangement 16 spatially arranges the groups of gated IVUS images 150 based on their determined longitudinal displacement relative to the spatial reference. Once all gated IVUS images 150 are positioned in this manner, the values of a pixel at position (x, y) may be seen as a 1-D signal (in Z), which has been sampled in different locations, which locations have been identified in the spatial repositioning of the gated groups of IVUS images 150 described above. The 3-D volume may now be interpolated by the processor arrangement 16 from the sampled pixel values using well-known interpolation techniques, which will not be explained in further detail for the sake of brevity only given that these techniques are well-known per se as previously explained. In operation 215, the processor arrangement 16 generates an output of the spatially ordered gated groups of IVUS images 150, which may take the form of a volume image of the region of interest 1 interpolated from these spatially ordered data groups of IVUS images 150. This output may be sent to the display device 18 for displaying the output thereon or alternatively may be sent to the data storage device 60 for retrieval at a later date. After the generation of this output by the processor arrangement 16, the method 200 may terminate.

Figure 3:
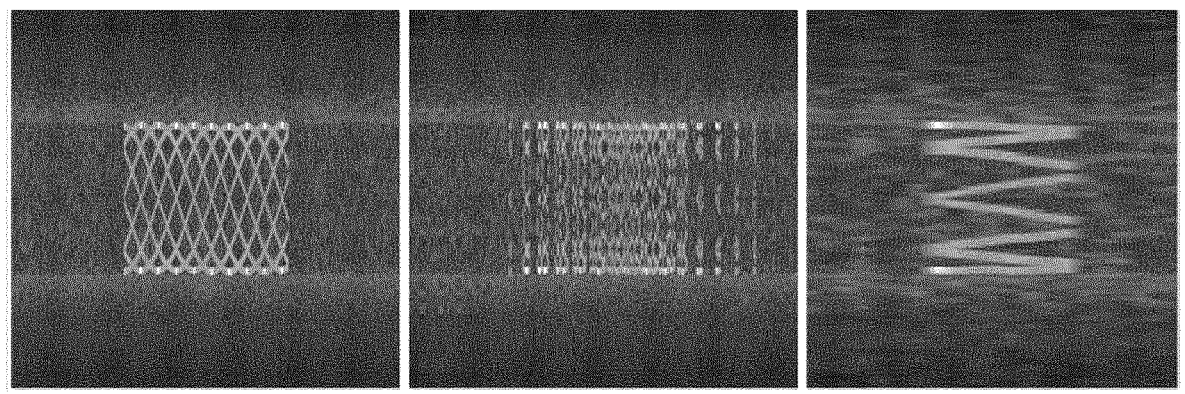
FIG. 3 shows images of a synthetic stent in a synthetic vessel captured in different manners.
Figure 9:
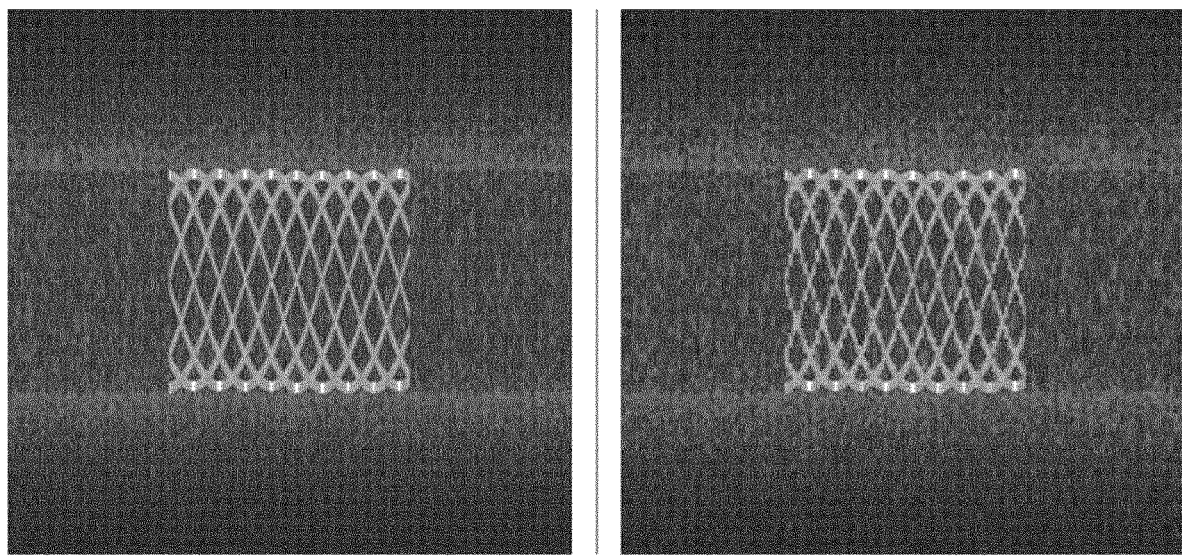
FIG. 9 shows images of a synthetic stent in a synthetic vessel captured and processed in different manners.

FIG. 9 shows a pair of images of a synthetic stent in a synthetic artery. The left-hand image is anatomically correct whereas the right-hand image is the interpolated image as generated from a plurality of spatially reordered groups of gated IVUS images 150. As can be seen, the interpolated image provides a high-quality approximation of the anatomically correct image, thereby demonstrating that the spatial reordering method 200 as described above can yield high-quality (volumetric) images using ungated IVUS images 150 that approximate anatomically correct images with a high degree of accuracy. It can be compared with the central image of FIG. 3, which shows the output without the invention being used.

The method 200 as implemented by the processor arrangement 16 of the image processing apparatus 10 optionally may be refined in a number of ways. In a preferred embodiment, the estimation of the displacement of a selected IVUS image group $V_i$ relative to the spatial reference $V_{ref}$ is not limited to deploying the same displacement to each IVUS image within the selected IVUS image group $V_i$. Such a common displacement may yield accurate results where the imaged region of interest of the patient's cardiovascular system exhibits few geometric variations, such that throughout the entire region of interest the magnitude of the cardiac cycle-induced displacement of the invasive medical device, e.g. the ultrasound probe 14, is largely constant at a particular phase of the patient's cardiac cycle. However, in many scenarios the imaged region of interest of the patient's cardiovascular system exhibits more substantial geometric variations that cause the cardiac cycle-induced displacement of the invasive medical device during a particular phase of the cardiac cycle to vary as a function of these geometric variations. Consequently, the displacement of the IVUS images within the selected IVUS image group $V_i$ relative to the spatial reference $V_{ref}$ typically is not constant.

Hence, as a first refinement, rather than applying a single longitudinal displacement in a systematic manner to all of the gated IVUS images 150 within a selected group $V_i$, the longitudinal displacement may be optimized separately for each individual IVUS image 150 within the group $V_i$. Such individualized displacements of the IVUS images 150 for instance may be deployed to compensate for local variations in the cardiac cycle-induced displacement of the invasive medical device 5. For example, gradual changes in the geometry or flexibility of the region of interest 1 of the cardiovascular system of the patient can cause such local variations. This may be leveraged by the processor arrangement 16 by applying optimized displacements of the IVUS images 150 that are gradually changed along the gated IVUS image group $V_i$ in a systematic manner in order to capture such gradual local variations. This may be achieved in any suitable manner; for example, the longitudinal displacement applied to the IVUS images 150 of the selected group $V_i$ may be modelled over a spline basis, after which the spline coefficients may be estimated. The nodes of such a spline may have any suitable density, e.g. a node may be provided every 2-5 mm. This is of course only a non-limiting example of a suitable motion estimation technique, and many more techniques will be immediately apparent to the skilled person. For example, the daemon-algorithm may be deployed by the processor arrangement 16, which may estimate one displacement value per IVUS image and subsequently filter these values with a Gaussian filter. In this manner, instead of estimating one unique displacement value to align $V_i$ and $V_{ref}$, a series of displacement coefficients may be obtained, which increases the flexibility of the mapping operation to ensure a more accurate mapping of the remaining IVUS image groups $V_i$ onto the spatial reference $V_{ref}$. Other techniques are readily available to the skilled person.

The determination of the optimal displacement distance for individual IVUS images within the selected IVUS image group $V_i$ further could be leveraged to correct for gating errors in a selected image group $V_i$ of gated IVUS images 150. In such an embodiment, a spline based model may be deployed in which the node density is a function of a phase of the patient's cardiac cycle associated with the selected IVUS image group $V_i$ in order to accurately and efficiently compensate for such gating errors.

As previously explained, gating errors during diastole are largely insensitive to cardiac cycle-induced displacement, whereas gating errors during systole can lead to large cardiac cycle-induced displacements of the IVUS image 150 exhibiting such a gating error. Therefore, for IVUS image groups associated with a (near-)diastolic phase of the patient's cardiac cycle, a more constrained (e.g. spline based) model of the longitudinal displacement may be used, (e.g. having a lower density of spline nodes, such as every 5 mm), whereas for IVUS image groups associated with a (near-)systolic phase of the patient's cardiac cycle, a more flexible (spline based model) of the longitudinal displacement may be used (e.g. having a higher density of spline nodes, such as every 2 mm). In such a manner, the estimated individual displacements of the IVUS images 150 in a selected IVUS image group $V_i$ may be used to compensate for gating errors. Again, many suitable alternatives to a spline-based approach will be immediately apparent to the skilled person.

In yet another refinement, the processor arrangement 16 may be adapted to identify a spatially neighboring group of gated IVUS images 150 to the spatial reference $V_{ref}$ and augment the spatial reference $V_{ref}$ by merging the spatially neighboring group of gated IVUS images 150 with the spatial reference $V_{ref}$, for example by merging each individual IVUS image 150 in the selected group $V_i$ with its counterpart image in the spatial reference $V_{ref}$ and spatially repositioning the merged IVUS images 150, e.g. by averaging the spatial position of an IVUS image 150 of the selected IVUS image group $V_i$ with the spatial position of the IVUS image 150 in the spatial reference $V_{ref}$ with which the image from $V_i$ is merged. In this manner, more information will be captured in the spatial reference $V_{ref}$ for the longitudinal motion compensation of subsequently selected groups of gated IVUS images 150. Although it is theoretically possible to selected any of the groups of gated IVUS images 150 for such a merging operation, by selecting a group that is spatially near to the spatial reference $V_{ref}$, two volumes or groups relating to diastole may be obtained that are more easily warped, such that as much information as possible can be captured in the spatial reference $V_{ref}$ to facilitate the spatial repositioning of the more difficult 'systolic' groups of gated IVUS images 150. This augmenting operation may be repeated a number of times in order to merge M of the N groups of gated IVUS images 150 in the spatial reference $V_{ref}$ (M<N) with the thus obtained spatial reference being used for the spatial repositioning of the remaining N-M groups of gated IVUS images 150 as explained in more detail above.

Another refinement that may be implemented is that after the spatial reordering of the temporal sequence 15 of IVUS images in operation 213, the processor arrangement 16 may return to operation 205 in which the spatially reordered temporal sequence 15 of IVUS images in operation 213 is again gated and the aforementioned operations 207, 209 and 211 are repeated to further improve the spatial repositioning of the IVUS images 150, in particular where the IVUS images are spatially repositioned in an individually optimized manner within a group $V_t$, as in this manner residual spatial positioning errors of the IVUS images 150 from previous spatial repositioning cycles can be further reduced. The processor arrangement 16 may repeat this iterative process for a fixed number of iterations, or alternatively the processor arrangement 16 may terminate the iterative process after comparing the spatially reordered sequence of IVUS images 150 of the actual iteration with the spatially reordered sequence of IVUS images 150 of the previous iteration, and terminate the iterative process if the difference between these spatially reordered sequences of IVUS images 150 falls below a defined threshold.

The aforementioned first main embodiment of the image processing apparatus 10, i.e. the implementation of the method 200 by its processor arrangement 16 has the advantage that no additional visualization techniques in addition to the IVUS imaging are required to create a spatially reliable 3-D image of the region of interest 1 of the cardiovascular system of the patient. In addition, no landmark detection in such a region of interest 1 in order to correctly position the IVUS images 150 relative to such detected landmarks. However, in a second main embodiment of the present invention, such additional visualization techniques and landmark detection are leveraged by the processor arrangement 16 to obtain the spatially reordered sequence of IVUS images 150.

At this point, it is noted that it is known from "Image-based Co-Registration of Angiography and Intravascular Ultrasound Images" by Wang et al in IEEE transactions on medical imaging, Vol. 32 (12), 2013 pages 2238-2249 to provide a system that detects a coronary branch under investigation in a reference angiography image. During pullback of the IVUS transducers, the system acquires both ECG-triggered fluoroscopy and IVUS images and automatically tracks the position of the medical devices in fluoroscopy. More specifically, both the ECG-triggered fluoroscopic images and the gated IVUS images are acquired in a time synchronized manner, with the fluoroscopic image acquisition being triggered at the end-diastole phase by ECG. However, it is far from trivial to expand such a gated approach to ungated IVUS image acquisition. For example, due to the cardiac phase-induced changes in the geometry of the cardiovascular system of the patient, extension of such mapping to ungated IVUS imaging yields a rather discontinuous (shaky or jumpy) visualization of the region of interest 1 when the individual ungated IVUS images 150 mapped to the angiographic images are shown in quick succession. Moreover, due to the changing geometry of the region of interest 1 during a cardiac cycle, spatial reordering of the temporal sequence 15 of ungated IVUS images 150 is not straightforward as the positions of the IVUS image slices 150 to each other are not clear cut.

Figure 10:
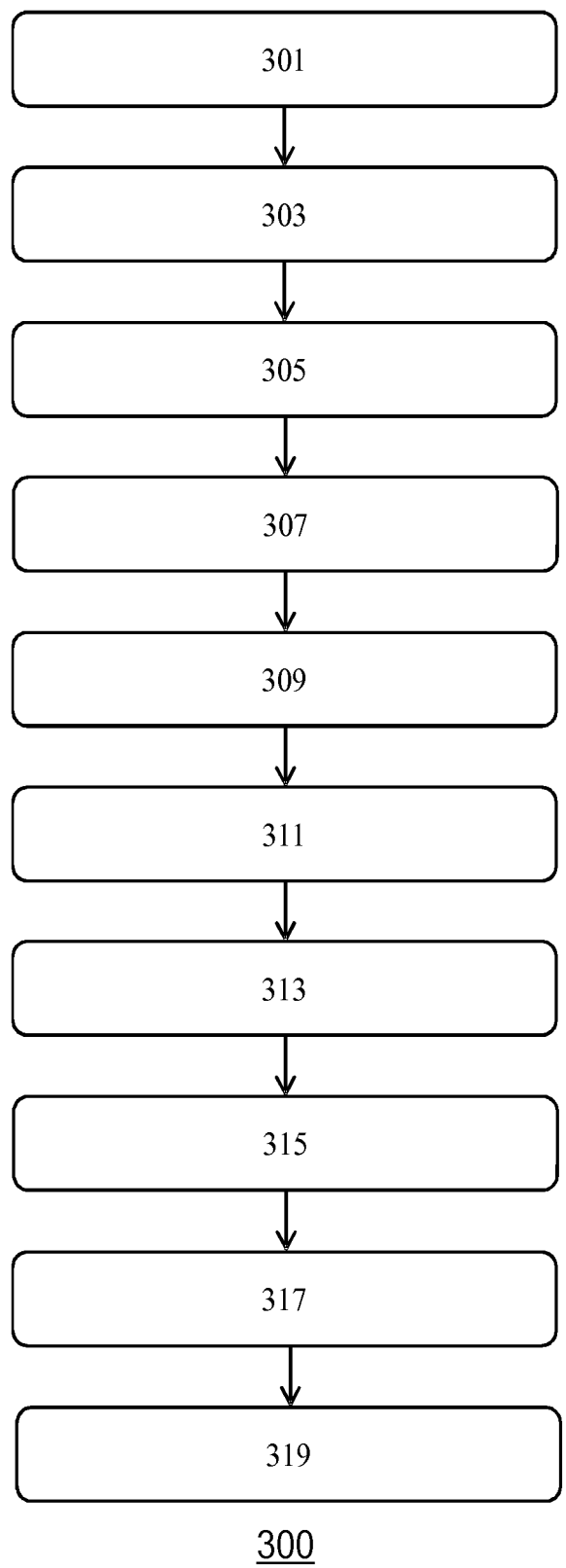
FIG. 10 is a flowchart of a method implemented by a processor arrangement of an image processing apparatus according to another embodiment.

At least some of these problems are addressed by the second main embodiment of the present invention, as will be described in more detail with the aid of FIG. 10, which depicts a flowchart of a method 300 implemented by the processor arrangement 16 for this purpose. In accordance with the method 300, the processor arrangement 16 in operation 301 receives a time-synchronized sequence of fluoroscopic images and a temporal sequence 15 of ungated IVUS images 150, with the latter being generated with the ultrasound probe 14 on the invasive medical device 5 as previously explained. For each IVUS image 150 acquired at a particular phase of the cardiac cycle, a fluoroscopic image is captured at the same time, i.e. at the same phase of the same cardiac cycle.

In operation 303, the processor arrangement 16 receives a sequence of angiographic images, which typically have been acquired under the same viewing angle as the fluoroscopic images, e.g. the same C-arm view, such that the fluoroscopic images can be easily mapped onto the angiographic images. As is well-known per se, angiographic images provide excellent detail of the topology of a patient's cardiovascular system, whereas fluoroscopic images provide excellent detail of the invasive medical device 5 within the patient's cardiovascular system. In order to further facilitate such mapping, the angiographic images are typically captured at approximately the same phases of the cardiac cycle as the fluoroscopic images, e.g. in a time-synchronized manner. The angiographic images may be acquired at any suitable point in time, such as prior to the acquisition of the fluoroscopic images and IVUS images 150. In an example embodiment, the processor arrangement 16 receives a previously recorded sequence of angiographic images from the data storage arrangement 60. It is noted for the same of completeness that although operation 303 is shown subsequent to operation 301 in FIG. 10, it will be understood from the foregoing that these operations may be executed in reverse order or even simultaneously by the processor arrangement 16.

Next, the processor arrangement 16 is adapted to proceed to operation 305 in which each of the IVUS images 150 are temporally matched (registered) to its fluoroscopic image counterpart, i.e. the fluoroscopic image captured at the same time or same phase of the cardiac cycle. In turn, the processor arrangement 16 spatially and temporally matches (registers) each of the fluoroscopic images to its angiographic image counterpart, e.g. using a cardiac road mapping algorithm.

As previously explained, the invasive medical device 5 including the ultrasound probe 14 is clearly visible in the fluoroscopic images, such that after the image-based co-registration the processor arrangement 16 detects the ultrasound probe 14 in each of the fluoroscopic images in operation 307. As is well-known per se, to this end the processor arrangement 16 may deploy hand-crafted detection filters that highlight features defining a signature of the appearance of the ultrasound probe 14 and/or part of the invasive medical device 5. Alternatively, the processor arrangement 16 may deploy learning algorithms to craft such a detection filter. Such techniques are well-known per se and are therefore not explained in further detail for the sake of brevity only. Consequently, by leveraging the mapping of the fluoroscopic images onto the angiographic images, the ultrasound probe 14 can be accurately positioned over a corresponding injected angiogram, i.e. an angiogram captured using an injected contrast agent and captured at the same cardiac phase of the fluoroscopic image in which the ultrasound probe 14 is visible. Hence, in this manner the processor arrangement obtains an association of each IVUS image 150 with a particular angiographic image as well as a spatial position of the ultrasound probe 14 within the angiographic image, e.g. expressed in terms of (x, y) pixel coordinates.

However, it should be understood that embodiments of the present invention are not limited to such cardiac road mapping algorithms. Alternatively, it may only be required to temporally map the fluoroscopic images with the angiographic images as full spatial co-registration of the fluoroscopic images with the angiographic images may not be required, given that only the position of the minimally invasive medical device 5 is of interest. For example, the injection catheter used to inject the minimally invasive medical device 5 into the patient's cardiovascular system may be detected both in the fluoroscopic images and the angiographic images, after which the distance of the minimally invasive medical device 5 to a reference point on the injection catheter is extracted from the fluoroscopic images after which the thus extracted distance is reported in the angiographic images. In this manner, the co-registration of the minimally invasive medical device 5 with the fluoroscopic images and the angiographic images can be achieved without (full) spatial co-registration of the fluoroscopic images and the angiographic images.

The processor arrangement 16 is further adapted to perform operation 309 of the method 300 in which the processor arrangement 16 extracts the pullback centreline of the invasive medical device 5 through the region of interest 1 of the patient's cardiovascular system. For example, the processor arrangement 16 may be adapted to evaluate the successive co-registered ultrasound probe 14 positioned in the angiographic images. The probe positions may be depicted as a dotted line over the relevant angiogram along the pullback centreline. This representation may be incomplete (i.e. some dots may be missing) and may further include potential outliers. The processor arrangement 16 constructs the centreline from this representation by joining more distal dots to more proximal dots with the constraints that the centreline has to pass close to as many dots (probe points) as possible whilst the centreline stays within the injected region of interest 1, e.g. a section of a coronary artery. This in practice corresponds to the generation of an energy map that reflects these constraints. The centreline may be propagated along the region of interest 1 using a suitable algorithm such as a suitably adapted fast marching algorithm.

The processor arrangement 16 is further adapted to perform operation 311 of the method 300 in which the processor arrangement 16 detects a plurality of anatomical landmarks (i.e. vessel landmarks) in each angiographic image using appropriately constructed detectors. As previously explained, the construction of such detector may be done manually or (semi-) automatically by the processor arrangement 16 using deep learning algorithms. Such techniques are well-known per se and will therefore not be explained in further detail for the sake of brevity. Such anatomical landmarks associated with the blood vessel of the patient may for instance include vessel bifurcation, stenosis, stents, and so on. Once the anatomical landmarks have been detected, the processor arrangement 16 may further deploy a distance filter such that only anatomical landmarks within a defined distance of the previously determined pullback centreline are retained, as only anatomical landmarks in the direct vicinity to the pullback centreline are likely to be of relevance.

The processor arrangement 16 subsequently evaluates the detected anatomical landmarks and associates identical landmarks across the plurality of angiographic images, e.g. by providing the same landmark in different angiographic images with the same label. The determination whether landmarks in different angiographic images are indeed the same may be made based on landmark type, local appearance, spatial location, and so on. The processor arrangement 16 is further adapted to discard those landmarks that are not present in each of the angiographic images, such that a set of landmarks common to all angiographic images remains. These common landmarks provide spatial waypoints through the region of interest 1 of the cardiovascular system of the patient, which may be used to spatially reorder the temporal sequence 15 of IVUS images 150.

To this end, the processor arrangement 16 is further adapted to perform operation 313 of the method 300 in which the processor arrangement 16 segments the pullback centreline in a plurality of segments, with each centreline segment being bound by a pair of spatially separated anatomical landmarks. An example centreline segment 6 is schematically depicted in FIG. 11, in which the centreline segment 6 is bound by spatially separated anatomical landmarks, here a first bifurcation 2 and a second bifurcation 2'. In this manner, the pullback centreline is segmented into a plurality of centreline segments that are coherent from one cardiac phase to another, such that these centreline segments may be used as a spatial reference for the spatial reordering of the temporally ordered IVUS images 150 by association of these IVUS images 150 with a location of the ultrasound probe 14 in the co-registered fluoroscopic images.

To this end, the processor arrangement 16 is further adapted to perform operation 315 of the method 300 in which the processor arrangement 16 determines the spatial position of the ultrasound probe 14 on a pullback centreline segment 6. The ultrasound probe 14 may appear in different locations on the pullback centreline segment 6, e.g. positions 7 and 9 in FIG. 11, in which case the spatial order of the IVUS images 150 associated with these different probe locations may be derived by determining the probe location on the pullback centreline segment 6 relative to its proximity to one of the anatomical landmarks that form the boundaries of the pullback centreline segment 6. For example, in FIG. 11 the location 7 may be determined to lie at 15% of the total length of the pullback centreline segment 6 from the bifurcation 2, whereas location 9 may be determined to lie at 65% of the total length of pullback centreline segment 6 from the bifurcation 2. In this manner, it can be determined that location 7 succeeds location 9 (assuming a pullback in the direction from bifurcation 2' to bifurcation 2) even if direct comparison between the co-registered fluoroscopic and angiographic images is not possible due to significant changes in the geometry of the region of interest 1 across different phases of the cardiac cycle as previously explained.

Upon determination of the locations of the ultrasound probe 14 along the respective pullback centreline segments, the processor arrangement 16 may perform operation 317 of the method 300 in which the processor arrangement 16 spatially reorders the temporal sequence 15 of ungated IVUS images 150 based on the determined positions of the ultrasound probe 14 along the respective pullback centreline segments, as each probe position is derived from a particular fluoroscopic image that is co-registered with a particular IVUS image 150, such that the IVUS image 150 can be associated with a particular probe location accordingly. Finally, in operation 319 the processor arrangement 16 generates an output of the spatially ordered gated groups of IVUS images 150, which may take the form of a volume image of the region of interest 1 interpolated from these spatially reordered IVUS images 150. This output may be sent to the display device 18 for displaying the output thereon or alternatively may be sent to the data storage device 60 for retrieval at a later date. After the generation of this output by the processor arrangement 16, the method 300 may terminate.

The image processing apparatus 10 according to embodiments of the present invention may be provided as a stand-alone apparatus. Alternatively, the image processing apparatus 10 may be provided together with the invasive medical device 5 such as a catheter or guide wire carrying an ultrasound probe 14 to form an IVUS imaging system. The above described embodiments of the methods 200 and 300 may be realized by computer readable program instructions embodied on a computer readable storage medium having, when executed on a processor arrangement of the ultrasound system 100, cause the processor arrangement to implement the method 200 and/or 300. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on.

The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, an ultrasound imaging apparatus 10 is adapted to retrieve the computer readable program instructions from such a computer readable storage medium and to create a new computer readable storage medium by storing the retrieved computer readable program instructions in a data storage arrangement 60, e.g. in a memory device or the like forming part of the data storage arrangement, which data storage arrangement is accessible to the processor arrangement 16 such that the processor arrangement 16 can retrieve the computer-readable program instructions from the data storage arrangement 60 for execution.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An image processing apparatus comprising a processor arrangement adapted to:
    receive image data corresponding to a region of interest of a patient's cardiovascular system, said image data comprising a temporal sequence of intravascular ultrasound images acquired at different phases of at least one cardiac cycle of said patient, said intravascular ultrasound images imaging overlapping volumes of the patient's cardiovascular system;
    implement a spatial reordering process of said temporal sequence of intravascular ultrasound images by:
        evaluating the temporal sequence of intravascular ultrasound images to select at least one spatial reference from said temporal sequence of intravascular ultrasound images without using a secondary imaging technique;
        estimating, based on the temporal sequence of intravascular ultrasound images, a distance to the at least one spatial reference for each of the intravascular ultrasound images of said temporal sequence; and
        reordering said temporal sequence of intravascular ultrasound images into a spatial sequence of intravascular ultrasound images based on the estimated distances; and generate an output comprising said spatial sequence of intravascular ultrasound images.

2. The image processing apparatus of claim 1, wherein the temporal sequence of intravascular ultrasound images covers a plurality of cardiac cycles, and wherein the processor arrangement is further adapted to implement said spatial reordering process by:
    gating said temporal sequence of intravascular ultrasound images into a plurality of intravascular ultrasound image groups, each group of the plurality of ultrasound image groups consisting of intravascular ultrasound images corresponding to approximately a same phase of a cardiac cycle; and
    selecting a first intravascular ultrasound image group of the plurality of intravascular image groups as the spatial reference;
    wherein estimating the distance from the spatial reference for each of the intravascular ultrasound images of said temporal sequence comprises, for each intravascular ultrasound image that is not in the first intravascular ultrasound image group, estimating said distance relative to an intravascular ultrasound image in the first intravascular ultrasound image group using a motion estimation algorithm.

3. The image processing apparatus of claim 2, wherein the motion estimation algorithm is adapted to estimate an optimal distance for each intravascular ultrasound image not in the first intravascular ultrasound image group relative to an intravascular ultrasound image in the first intravascular ultrasound image group.

4. The image processing apparatus of claim 2, wherein the processor arrangement is further adapted to select the first intravascular ultrasound image group as the spatial reference based on the first intravascular ultrasound image group being captured during a diastolic phase.

5. The image processing apparatus of claim 2, wherein the processor arrangement is further adapted to estimate the distance from the spatial reference for each intravascular ultrasound image not in the first intravascular ultrasound image group by:
    identifying a spatially neighboring intravascular ultrasound image group to the first intravascular ultrasound image group; and
    generating an augmented spatial reference by merging the spatially neighboring intravascular ultrasound image group with the first intravascular ultrasound image group; and
    spatially repositioning the intravascular ultrasound images of the augmented spatial reference.

6. The image processing apparatus of claim 2, wherein the processor arrangement is further adapted to implement said spatial reordering process in an iterative manner on the spatial sequence of intravascular ultrasound images.

7. The image processing apparatus of claim 2, wherein the processor arrangement is further adapted to apply a motion compensation algorithm to the intravascular ultrasound images of said temporal sequence prior to gating the intravascular ultrasound images into the plurality of intravascular ultrasound image groups.

8. The image processing apparatus of claim 1, wherein the processor arrangement is further configured to:
receive secondary image data comprising:
a temporal sequence of fluoroscopic images of said region of interest captured under a viewing angle in which an invasive medical device used to capture the temporal sequence of intravascular ultrasound images is visible; and
a temporal sequence of angiographic images of said region of interest captured under said viewing angle, wherein each angiographic image is captured at approximately a same phase of the at least one cardiac cycle as a corresponding fluoroscopic image of the temporal sequence of fluoroscopic images;
temporally register each intravascular ultrasound image of the temporal sequence of intravascular ultrasound images to a fluoroscopic image of the temporal sequence of fluoroscopic images;
temporally register each fluoroscopic image of the temporal sequence of fluoroscopic images to an angiographic image of the temporal sequence of angiographic images;
identify the invasive medical device within the patient's cardiovascular system in said fluoroscopic images;
extract a path of the identified invasive medical device through the patient's cardiovascular system from the registered fluoroscopic and angiographic images;
identify a set of anatomical landmarks from the angiographic images of the temporal sequence of angiographic images that are common to said angiographic images;
divide the extracted path of the identified invasive medical device through the patient's cardiovascular system into a plurality of path segments, wherein each path segment is bound by a neighboring pair of said anatomical landmarks; and
reorder, at least in part, said temporal sequence of intravascular ultrasound images into a spatial sequence of intravascular ultrasound images based on a distance of an intravascular ultrasound image from said temporal sequence of intravascular ultrasound images along a path segment of the plurality of path segments to at least one of the anatomical landmarks binding said path segment.

9. The image processing apparatus of claim 8, wherein the processor arrangement is further adapted to spatially and temporally register each fluoroscopic image of the temporal sequence of fluoroscopic images to an angiographic image of the temporal sequence of angiographic images using a cardiac roadmapping algorithm.

10. The image processing apparatus of claim 8, wherein the processor arrangement is further adapted to extract the path of the invasive medical device through the patient's cardiovascular system from the temporally registered fluoroscopic and angiographic images by extracting a centerline of said path through the patient's cardiovascular system.

11. The image processing apparatus of claim 10, wherein the processor arrangement is further adapted to deploy a distance filter such that only anatomical landmarks within a defined distance of the centerline are included in the set of anatomical landmarks.

12. The image processing apparatus of claim 8, wherein the processor arrangement is further adapted to identify the set of anatomical landmarks using at least one deep learning algorithm.

13. The image processing apparatus of claim 1, wherein the processor arrangement is further adapted to determine, for each ultrasound image, a cardiac cycle phase based on the temporal sequence of intravascular ultrasound images.

14. The image processing apparatus of claim 1, wherein the processor arrangement is further adapted to:
detect motion of one or more substances in the temporal sequence of intravascular ultrasound images; and
produce an image depicting the motion of the one or more substances.

15. A computer-implemented method of processing a temporal sequence of intravascular ultrasound images acquired at different phases of at least one cardiac cycle, the method comprising:
receiving image data corresponding to a region of interest of a patient's cardiovascular system, said image data comprising said temporal sequence of intravascular ultrasound images, said intravascular ultrasound images imaging overlapping volumes of the patient's cardiovascular system;
implementing a spatial reordering process of said temporal sequence of intravascular ultrasound images by:
evaluating the temporal sequence of intravascular ultrasound images to select at least one spatial reference from said temporal sequence of intravascular ultrasound images without using a secondary imaging technique;
estimating, based on the temporal sequence of ultrasound images, a distance to the at least one spatial reference for each of the intravascular ultrasound images of said temporal sequence; and
reordering said temporal sequence of intravascular ultrasound images into a spatial sequence of intravascular ultrasound images based on the estimated distances; and
generating an output comprising said spatial sequence of intravascular ultrasound images.

16. The computer-implemented method of claim 15, wherein the temporal sequence of intravascular ultrasound images covers a plurality of cardiac cycles, and the method is further adapted to, implement said spatial reordering process by:
gating said temporal sequence of intravascular ultrasound images into a plurality of intravascular ultrasound image groups, each group of the plurality of ultrasound image groups consisting of intravascular ultrasound images corresponding to approximately a same phase of a cardiac cycle; and
selecting a first intravascular ultrasound image group of the plurality of intravascular image groups as the spatial reference;
wherein estimating the distance from the spatial reference for each of the intravascular ultrasound images of said temporal sequence comprises, for each intravascular ultrasound image that is not in the first intravascular ultrasound image group, estimate said distance relative to an intravascular ultrasound image in the first intravascular ultrasound image group using a motion estimation algorithm.

17. The computer-implemented method of claim 16, further comprising implementing said spatial reordering process in an iterative manner on the spatial sequence of intravascular ultrasound images.

18. The computer-implemented method of claim 15, further comprising:
- receiving secondary image data corresponding to the region of interest of the patient's cardiovascular system, the secondary image data including:
  - a temporal sequence of fluoroscopic images of said region of interest captured under a viewing angle in which an invasive medical device used to capture the temporal sequence of intravascular ultrasound images is visible; and
  - a temporal sequence of angiographic images of said patient region of interest captured under said viewing angle, wherein each angiographic image is captured at approximately a same phase of the at least one cardiac cycle as a corresponding fluoroscopic image of the temporal sequence of fluoroscopic images;

the method further comprising:
- temporally registering each intravascular ultrasound image of the temporal sequence of intravascular ultrasound images to a fluoroscopic image of the temporal sequence of fluoroscopic images;
- temporally registering each fluoroscopic image of the temporal sequence of fluoroscopic images to an angiographic image of the temporal sequence of angiographic images;
- identifying the invasive medical device within the patient's cardiovascular system in the fluoroscopic images;
- extracting a path of the identified invasive medical device through the patient's cardiovascular system relative to the registered fluoroscopic and angiographic images;
- identifying a set of anatomical landmarks from the angiographic images of the temporal sequence of angiographic images that are common to said angiographic images;
- dividing the extracted path of the identified invasive medical device through the patient's cardiovascular system into a plurality of path segments, each defining a spatial reference, wherein each path segment is bound by a neighboring pair of said anatomical landmarks; and
- reordering, at least in part, said temporal sequence of intravascular ultrasound images into a spatial sequence of intravascular ultrasound images based on the distance of an intravascular ultrasound image from said temporal sequence of intravascular ultrasound images along a path segment of the plurality of path segments to at least one of the anatomical landmarks binding said path segment.

19. A computer program product comprising a computer readable storage medium having computer readable program instructions embodied therewith for, when executed on a processor arrangement of an image processing apparatus, cause the processor arrangement to implement the method of claim 15.

20. The computer implemented method of claim 15, further comprising:
- detecting motion of one or more substances in the temporal sequence of intravascular ultrasound images; and
- producing an image depicting the motion of the one or more substances.

* * * * *